(12) United States Patent
Yi

(10) Patent No.: US 7,664,228 B2
(45) Date of Patent: Feb. 16, 2010

(54) X-RAY IMAGING APPARATUS AND DETECTOR PANEL

(75) Inventor: Fan Yi, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/358,747

(22) Filed: Jan. 23, 2009

(65) Prior Publication Data

US 2009/0207973 A1  Aug. 20, 2009

(30) Foreign Application Priority Data

Feb. 15, 2008  (CN) .................. 2008 1 0009885

(51) Int. Cl.
H05G 1/10 (2006.01)
H05G 1/64 (2006.01)

(52) U.S. Cl. ...................... 378/101; 378/98.8

(58) Field of Classification Search ......... 378/101–103, 378/98.8
See application file for complete search history.

(56) References Cited

U.S. PATENT DOCUMENTS

| | | | |
|---|---|---|---|
| 4,681,227 A | 7/1987 | Tamura et al. | |
| 4,922,105 A | 5/1990 | Hosoi | |
| 5,081,543 A | 1/1992 | Romandi | |
| 5,514,873 A | 5/1996 | Schulze-Ganzlin et al. | |
| 5,808,376 A * | 9/1998 | Gordon et al. | ................ 307/66 |
| 5,877,501 A | 3/1999 | Ivan et al. | |
| 5,912,941 A | 6/1999 | Schmitt | |
| 6,091,982 A | 7/2000 | Reinke et al. | |
| 6,205,119 B1 | 3/2001 | Kaczynski | |
| 6,575,624 B2 | 6/2003 | Noegel et al. | |
| 6,700,126 B2 | 3/2004 | Watanabe | |
| 7,046,764 B1 * | 5/2006 | Kump | ................ 378/117 |
| 7,078,703 B2 | 7/2006 | Watanabe | |
| 7,127,032 B1 * | 10/2006 | Kump | ................ 378/117 |
| 7,164,137 B2 | 1/2007 | Hayashida | |
| 7,189,972 B2 | 3/2007 | Ertel et al. | |
| 7,317,190 B2 | 1/2008 | Ertel et al. | |
| 7,342,998 B2 | 3/2008 | Kump et al. | |
| 7,396,159 B2 | 7/2008 | Utschig et al. | |
| 7,435,967 B2 | 10/2008 | Ertel et al. | |
| 2002/0150214 A1 | 10/2002 | Spahn | |

FOREIGN PATENT DOCUMENTS

JP  2002-336227  11/2002

* cited by examiner

Primary Examiner—Irakli Kiknadze
(74) Attorney, Agent, or Firm—Armstrong Teasdale LLP

(57) ABSTRACT

A detector panel incorporates an X-ray detector, an electronic circuit for interface, and a battery for power supply, and also includes a measurement device for measuring the remaining power of the battery, and a determination device for determining if the operation is executable, based on the comparison between the remaining power of the battery and the threshold defined in accordance with the required power for operating the X-ray detector and the electronic circuit.

20 Claims, 10 Drawing Sheets

406

| address | content |
|---|---|
| Basic NIO #1 | Δ RSOC #1 |
| Basic NIO #2 | Δ RSOC #2 |
| ... | ... |
| Basic NIO #n | Δ RSOC #n |

FIG. 7

X-RAY IMAGING APPARATUS AND DETECTOR PANEL

CROSS REFERENCE TO RELATED APPLICATIONS

This application claims the benefit of Chinese Patent Application No. 200810009885.6 filed Feb. 15, 2008, which is hereby incorporated by reference in its entirety.

BACKGROUND OF THE INVENTION

The embodiments described herein relate to an X-ray imaging apparatus and a detector panel, more specifically, the present invention is related to an X-ray imaging apparatus having a system console including an X-ray emitter and a control circuit, and a detector panel including an X-ray detector, an electronic circuit for interface, and a battery for power supply, as well as to a detector panel for the X-ray imaging apparatus.

There is a mobile type X-ray imaging apparatus as a sort of X-ray imaging apparatus. This type of X-ray imaging apparatus is comprised of a movable system console and a portable detector panel. The system console comprises an X-ray emission device and a controller device, while the detector panel comprises an X-ray detector, a signal processing circuit for interface, and a battery for power supply.

For X-ray imaging, the X-ray imaging apparatus is moved to the sickroom of a patient. To take images in the sickroom, the detector panel is placed on the imaging location of the patient, and the X-ray is emitted thereto from the opposite side. The X-ray signal, which is detected by the detector panel, is transmitted via a wired or wireless line to the system console (for example, see Japanese Unexamined Patent Publication No. 2002-336227 (para. 0017 to 0020, and FIG. 1)

BRIEF DESCRIPTION OF THE INVENTION

Since the power supplied from the built-in battery in the detector panel is consumed and decreased by the X-ray detector and the interface, the shortage of the power or the interruption of operation may occur when there is left insufficient power. In such a case the image taken prior to the shortage may become futile. The imaging should be taken again from the scratch after recharging or replacing the battery.

Accordingly, embodiments described herein provide an X-ray imaging apparatus which is capable of preventing the interruption of operation caused by the shortage of power by the battery, and a detector panel for use in the X-ray imaging apparatus.

The present invention for solving the problem in a first aspect provides an X-ray imaging apparatus having: a system console including an X-ray emitter and a control circuit; and a detector panel including an X-ray detector, an electronic circuit for interface, and a battery for power supply, the detector panel comprising: a measurement device for measuring the electric power left in the battery; and a determination device for determining whether or not the execution of the operation is possible based on the comparison of the power left in the battery with the threshold defined in accordance with the required power for operating the X-ray detector and the electronic circuit.

The present invention for solving the problem in a second aspect provides an X-ray imaging apparatus set forth in the first aspect described above, in which the operation is not interruptible.

The present invention for solving the problem in a third aspect provides an X-ray imaging apparatus set forth in the first or second aspect described above, further comprising a memory device for storing the required power for each unit operation constituting the operation.

The present invention for solving the problem in a fourth aspect provides an X-ray imaging apparatus set forth in the third aspect further comprising: a memory update device for updating stored values in the memory device.

The present invention for solving the problem in a fifth aspect provides an X-ray imaging apparatus set forth in the third or fourth aspect described above, further comprising: a first threshold calculation device for determining the initial value of the threshold based on the stored values prior to initial execution of the operation.

The present invention for solving the problem in a sixth aspect provides an X-ray imaging apparatus set forth in the first or second aspect described above, further comprising: a second threshold calculation device for determining the latest threshold based on the measurement value of the power left before and after the execution of the operation.

The present invention for solving the problem in a seventh aspect provides an X-ray imaging apparatus set forth in the sixth aspect described above further comprising: a threshold update device for updating the threshold so far by using the latest threshold.

The present invention for solving the problem in an eighth aspect provides an X-ray imaging apparatus set forth in the seventh aspect described above, wherein the update of the threshold is performed when the latest threshold is larger than the prior threshold.

The present invention for solving the problem in a ninth aspect provides an X-ray imaging apparatus set forth in the first aspect described above, wherein the comparison is performed prior to the execution of the operation.

The present invention for solving the problem in a tenth aspect provides an X-ray imaging apparatus set forth in the ninth aspect described above, wherein the comparison is also performed after the execution of the operation.

The present invention for solving the problem in an eleventh aspect provides a detector panel having an X-ray detector, an electronic circuit for interface, and a battery for power supply, comprising: a measurement device for measuring the power left in the battery; and a determination device for determining whether or not the operation is executable based on a comparison of the power left in the battery with the threshold determined based on the required power for operating the X-ray detector and the electronic circuit.

The present invention for solving the problem in a twelfth aspect provides a detector panel set forth in the eleventh aspect described above, wherein the operation is not interruptible.

The present invention for solving the problem in a thirteenth aspect provides a detector panel set forth in the eleventh or twelfth aspect described above, further comprising: a memory device for storing the required power for each unit operation constituting the operation.

The present invention for solving the problem in a fourteenth aspect provides a detector panel set forth in the thirteenth aspect described above, further comprising: a memory update device for updating stored values in the memory device.

The present invention for solving the problem in a fifteenth aspect provides a detector panel set forth in the thirteenth or fourteenth aspect described above, further comprising: a first threshold calculation device for determining the initial value of the threshold based on the stored values prior to initial execution of the operation.

The present invention for solving the problem in a sixteenth aspect provides a detector panel set forth in the eleventh or twelfth aspect described above, further comprising: a second threshold calculation device for determining the latest threshold based on the measurement value of the power left before and after the execution of the operation.

The present invention for solving the problem in a seventeenth aspect provides a detector panel set forth in the sixteenth aspect described above, further comprising: a threshold update device for updating the threshold so far by using the latest threshold.

The present invention for solving the problem in an eighteenth aspect provides a detector panel set forth in the seventeenth aspect described above, wherein the update of the threshold is performed when the latest threshold is larger than the prior threshold.

The present invention for solving the problem in a nineteenth aspect provides a detector panel set forth in the eleventh aspect described above, wherein the comparison is performed prior to the execution of the operation.

The present invention for solving the problem in a twentieth aspect provides a detector panel set forth in the nineteenth aspect described above, wherein the comparison is also performed after the execution of the operation.

In accordance with the present invention, in the first aspect, the X-ray imaging apparatus has a system console including an X-ray emitter and a control circuit, and a detector panel including an X-ray detector, an electronic circuit for interface, and a battery for power supply, the detector panel comprising a measurement device for measuring the electric power left in the battery, and a determination device for determining whether or not the execution of the operation is possible based on the comparison of the power left in the battery with the threshold defined in accordance with the required power for operating the X-ray detector and the electronic circuit, thereby realizing an X-ray imaging apparatus which is capable of preventing the interruption of operation caused by the shortage of battery power to be achieved.

In accordance with the present invention, in the eleventh aspect, the detector panel having an X-ray detector, an electronic circuit for interface, and a battery for power supply, including a measurement device for measuring the power left in the battery; and a determination device for determining whether or not the operation is executable based on a comparison of the power left in the battery with the threshold determined based on the required power for operating the X-ray detector and the electronic circuit, thereby realizing a detector panel for an X-ray imaging apparatus which is capable of preventing the interruption of operation caused by the shortage of battery power to be achieved.

In accordance with the present invention, in the second or twelfth aspect, the operation is not interruptible, thereby realizing obtaining the optimum threshold for determining whether or not to execute the operation.

In accordance with the present invention, in the third or thirteenth aspect, a memory device for storing the required power for each unit operation constituting the operation is incorporated so that the required power for the non-interruptible operation may be readily determined.

In accordance with the present invention, in the fourth or fourteenth aspect, a memory update device for updating stored values in the memory device is incorporated, thereby allowing the stored values to be held up-to-date.

In accordance with the present invention, in the fifth or fifteenth aspect, a first threshold calculation device for determining the initial value of the threshold based on the stored values prior to initial execution of the operation is incorporated, thereby obtaining the optimum threshold for the operation for the first time.

In accordance with the present invention, in the sixth or sixteenth aspect, a second threshold calculation device for determining the latest threshold based on the measurement value of the power left before and after the execution of the operation is incorporated, thereby obtaining the threshold accommodating with the battery status.

In accordance with the present invention, in the seventh or seventeenth aspect, a threshold update device for updating the threshold so far by using the latest threshold is incorporated, thereby maintaining the latest threshold accommodating with the battery status.

In accordance with the present invention, in the eighth or eighteenth aspect, the update of the threshold is performed when the latest threshold is larger than the prior threshold, thereby reasonably updating the threshold.

In accordance with the present invention, in the ninth or nineteenth aspect, the comparison is performed prior to the execution of the operation, thereby preventing beforehand the interruption of operation caused by the shortage of battery power from happening.

In accordance with the present invention, in the tenth or twentieth aspect, the comparison is also performed after the execution of the operation, thereby preventing the interruption of operation caused by the shortage of battery power form happening, resulting from the operation thereafter.

BRIEF DESCRIPTION OF THE DRAWINGS

FIG. 7 is a schematic diagram illustrating a $\Delta$RSOC table;

DETAILED DESCRIPTION OF THE INVENTION

Various embodiments of the present invention will be described in greater details herein below with reference to the accompanying drawings. It should be noted here that the present invention is not considered to be limited to the embodiments described herein.

Figure 1:
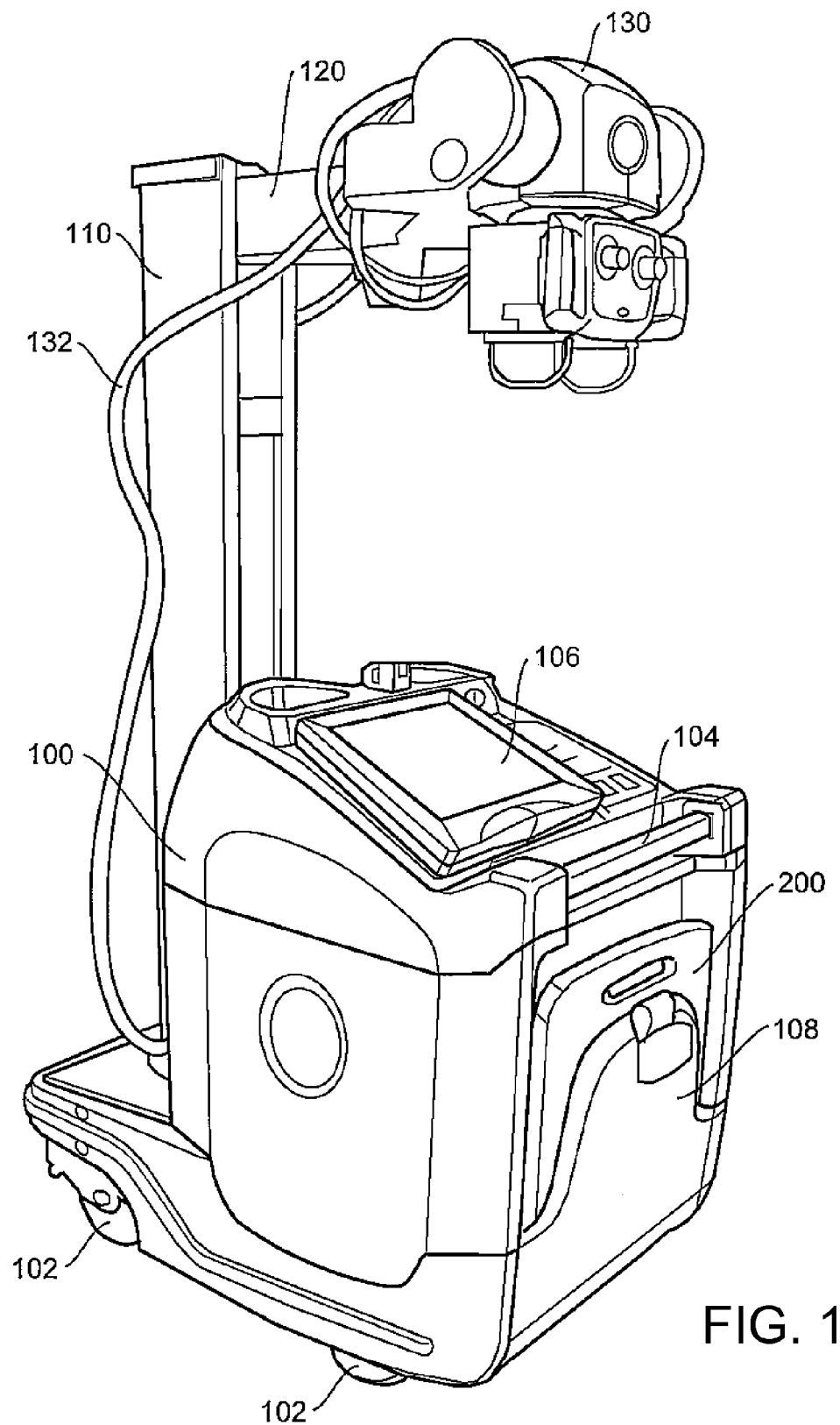
FIG. 1 is a schematic diagram illustrating the appearance of an X-ray imaging apparatus.
Figure 2:
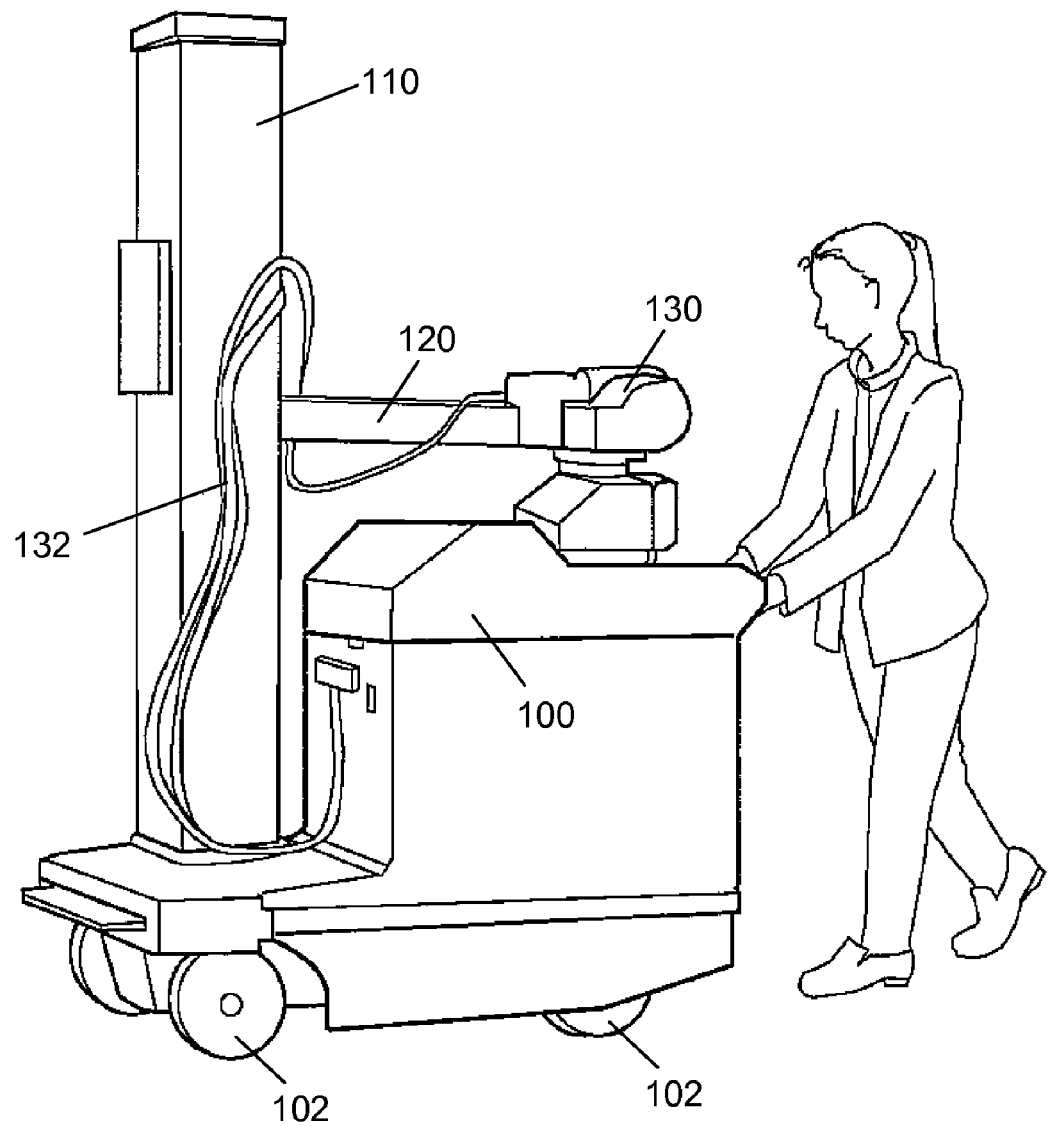
FIG. 2 is a schematic diagram illustrating the operation scene of the X-ray imaging apparatus shown in FIG. 1.

Now referring to FIG. 1, there is shown the appearance of an X-ray imaging apparatus. The arrangement of the apparatus indicates an exemplary X-ray imaging apparatus.

As shown in FIG. 1, the apparatus has a system console 100. The system console 100 is an example of system console in accordance with the present invention. The system console 100 is a structure of approximately cubic box-shape, housing the electronic circuit for controlling the imaging therein. The electronic circuit for controlling the imaging is an example of the control circuit in accordance with the present invention.

The system console 100 has casters 102 for moving at the bottom of the structure, and a handle 104 for pushing by hand. The apparatus thereby is a relocatable X-ray imaging apparatus which is capable of desirably moving to anywhere.

The top surface of the system console 100 is a control panel 106, which includes man machine communication equipment, such as for example a graphic display, a keyboard, and so on.

At the back side of the system console 100 there is provided a vertical column 110, and an X-ray emitter 130 is attached at the end of an arm 120 horizontally extending from the vertical column 110. The X-ray emitter 130 generates X-ray by using a high voltage power supplied from the system console 100 through a cable 132. The X-ray emitter 130 is an example of X-ray emission device in accordance with the present invention.

The X-ray emitter 130 is capable of changing its direction at the end of the arm 120. The arm 120 is vertically movable along with the vertical column 110, which vertical column 110 swings (spins) around the longitudinal axis of the vertical column 110.

The apparatus has a detector panel 200. The detector panel 200 is an approximately square, box-shaped structure which is separated from the system console 100 so as to be portable. The detector panel 200 is housed in a storage box 108 at the front of the system console 100 when not in use, and is taken out from the storage box 108 to use when taking images.

The detector panel 200 is an example of the best mode for carrying out the invention. The arrangement of the detector panel 200 indicates an exemplary best mode for carrying out the invention with respect to the detector panel.

Figure 3:
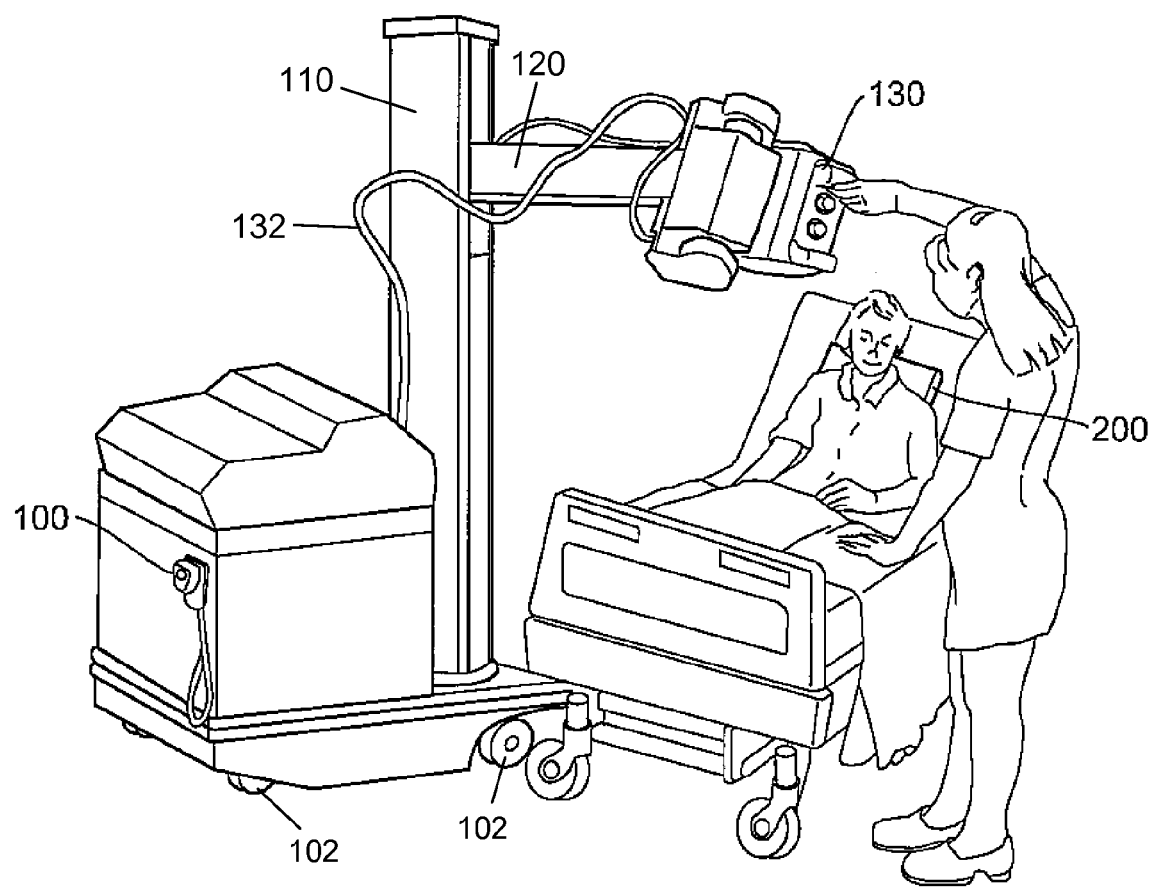
FIG. 3 is a schematic diagram illustrating the operation scene of imaging a patient by the X-ray imaging apparatus shown in FIG. 1.

Now referring to FIG. 3, there is shown a schematic diagram of the apparatus in use. As shown in FIG. 3, the apparatus is operated in a sickroom. The X-ray imaging is conducted by placing the detector panel 200 for example at the back of a patient, and by emitting X-ray from the X-ray emitter 130 from the front side of the patient. The X-ray signal detected by the detector panel 200 is transmitted to the system console 100 through a wireless link.

Figure 4:
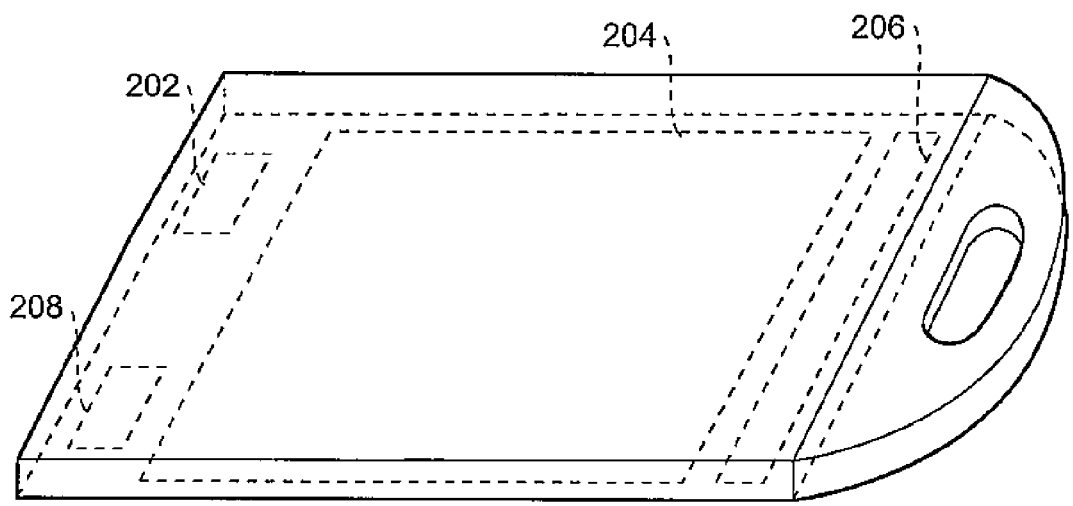
FIG. 4 is a schematic diagram illustrating the configuration of a detector panel.

Now referring to FIG. 4 there is shown a basic arrangement of the detector panel 200. As shown in FIG. 4, the detector panel 200 has a battery 202, an X-ray detector 204, an interface circuit 206, and a circuit for operation management 208.

The battery 202 is the power supply for the detector panel 200, which supplies power to the X-ray detector 204, the interface circuit 206, and the circuit for operation management 208. The battery 202 is a rechargeable battery.

The battery 202 is an exemplary battery for power supply in accordance with the present invention. The X-ray detector 204 is an exemplary X-ray detector in accordance with the present invention. The interface circuit 206 is an exemplary electronic circuit for interface in accordance with the present invention.

The X-ray detector 204 is a two-dimensional X-ray detector, which detects X-ray by each of a number of X-ray detector elements arranged in a matrix array. The interface circuit 206 transmits and receives for the system console 100. The detected signal from the X-ray detector 204 is transferred from the interface circuit 206 to the system console 100 through a wireless link.

The circuit for operation management 208 manages the operation of the X-ray detector 204 and the interface circuit 206. The circuit for operation management 208 determines whether or not the power left in the battery 202 is sufficient for normally operating the X-ray detector 204 and the interface circuit 206, and determines whether the operation is allowed or not.

Figure 5:
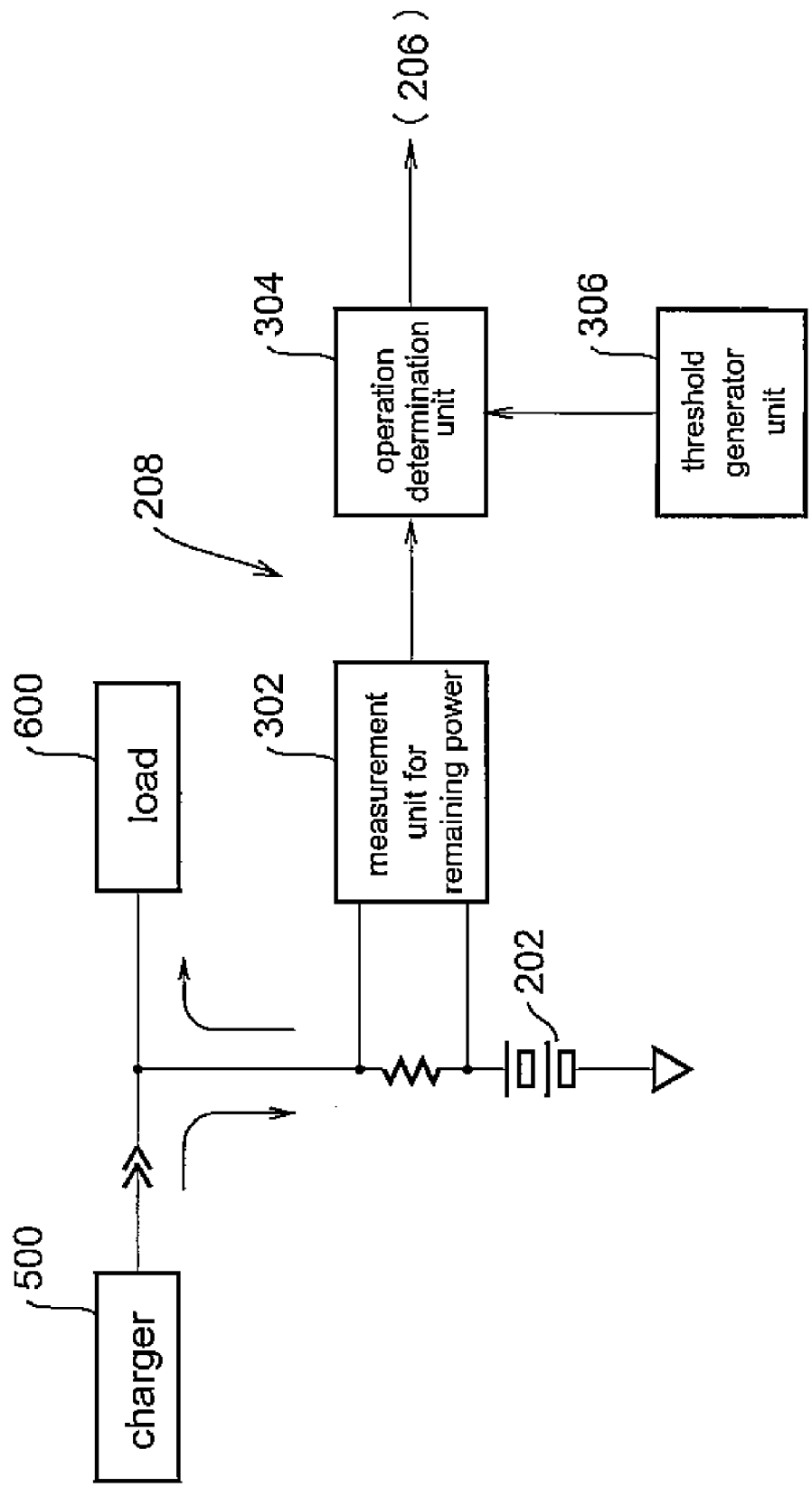
FIG. 5 is a schematic block diagram illustrating an operation management circuit.

Now referring to FIG. 5 there is shown a schematic block diagram illustrating the circuit for operation management 208. As shown in FIG. 5, the circuit for operation management 208 has a measurement unit for remaining power 302. The measurement unit for remaining power 302 measures the power left in the battery 202. The power left in the battery 202 will be referred to as simply "remaining power" herein below. The measurement unit for remaining power 302 is an exemplary measurement device in accordance with the present invention.

The measurement of the remaining power is based on the current for recharging and discharging the battery 202. The charging current flows from the charger 500 into the battery 202, the discharging current flows from the battery 202 to the load 600 when the X-ray detector 204, and the interface circuit 206 are in operation or in stand-by. The load 600 is the collective designation of the X-ray detector 204, the interface circuit 206, and the circuit for operation management 208.

The remaining power may be measured as the difference between the integrated value of the recharging current and the integrated value of the discharging current. To measure, for example, a known Coulomb counter or a known battery gas gauge may be used.

The measurement value of the remaining power may be indicated by for example the relative state of charge (RSOC). The relative state of charge will be referred to as simply RSOC herein below. The unit for the RSOC is %, and 100% indicates the relative state of completed charge, and 0% indicates the relative state of complete discharge. The measurement value of the remaining power may also be indicated by any appropriate unit such as feedable time, instead of the RSOC.

The measurement value of the remaining power is input to an operation determination unit 304. The operation determination unit 304 is also input with the threshold from a threshold generator unit 306. The operation determination unit 304 compares the measurement value of the remaining power with the threshold, and determines whether or not the operation of the X-ray detector 204 and the interface circuit 206 is acceptable, in accordance with the quantity of the remaining power with respect to the threshold. The operation determination unit 304 is an exemplary determination device in accordance with the present invention.

The output signal from the operation determination unit 304 is transferred from the interface circuit 206 to the system console 100, and is also displayed on an appropriate display placed on the detector panel 200. The display may be a light emitting display such as LED (light emitting diode).

Figure 6:
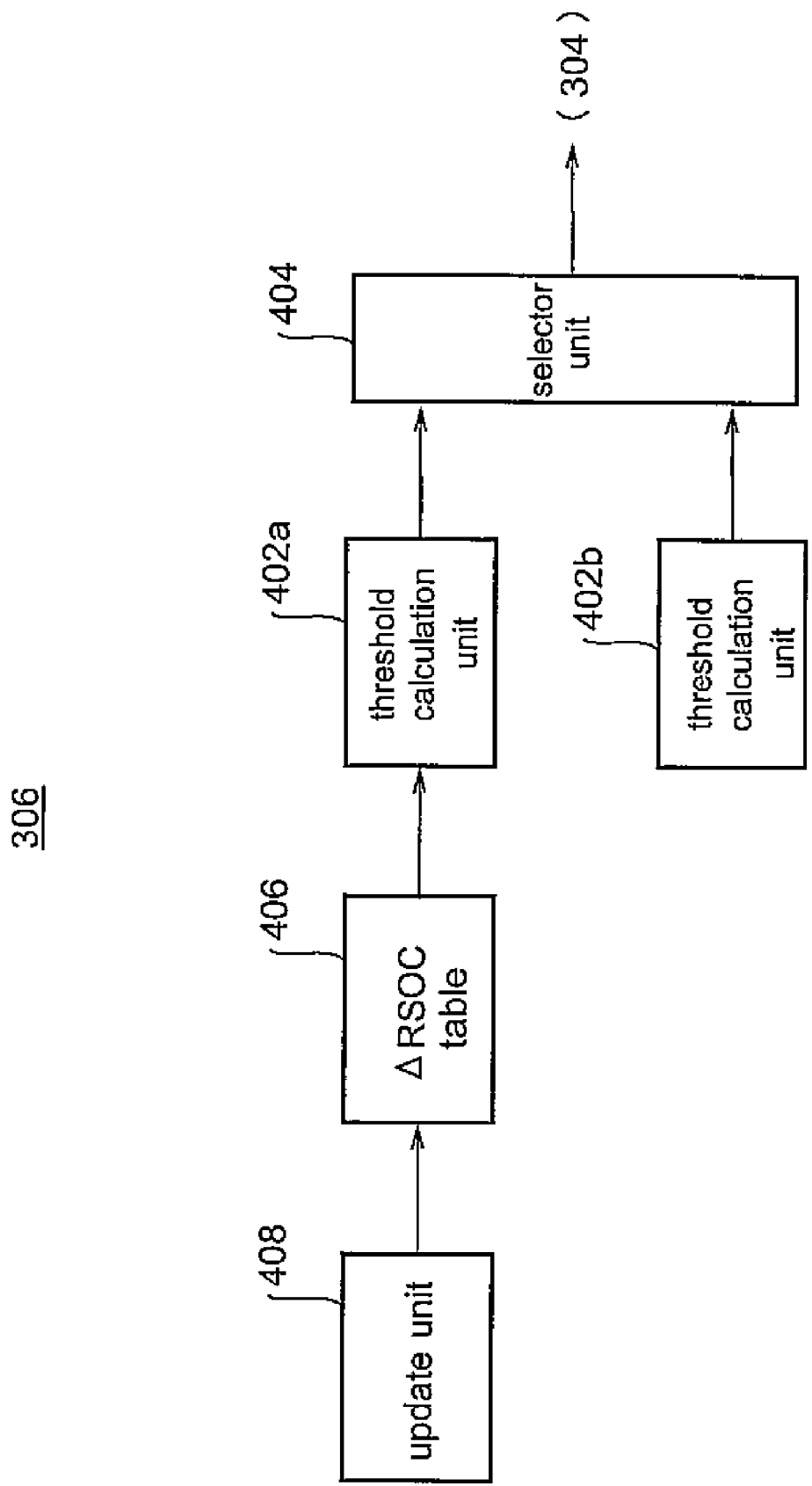
FIG. 6 is a schematic block diagram illustrating a threshold generator unit.

Now referring to FIG. 6 there is shown a schematic block diagram of the threshold generator unit 306. As shown in FIG. 6 the threshold generator unit 306 includes two threshold calculation units 402a and 402b. The threshold calculation units 402a and 402b calculates two thresholds. Either one of thus calculated two thresholds is output through the selector unit 404.

The threshold calculation unit 402a is an example of the first threshold calculation device in accordance with the present invention. The threshold calculation unit 402b is an example of the second threshold calculation device in accordance with the present invention. The selector unit 404 is an example of the threshold update device in accordance with the present invention.

The threshold calculation by the threshold calculation units 402a and 402b is performed based on the required power for performing the predetermined operation by the X-ray detector 204 and the interface circuit 206. The predetermined operation is the non-interruptible operation (NIO). The non-interruptible operation is a series of operation in which the imaging data may become invalid if interrupted. The non-interruptible operation will be referred to as NIO herein below.

The NIO is the operation from one single X-ray exposure and the acquisition of data to the transfer complete of the acquired data, in the simple X-ray imaging, and is the operation from a plurality of X-ray exposures and the data acquisition to the transfer complete of the acquired data, in the fluoroscopy.

The NIO is defined by the imaging condition configured by the user, i.e., a combination of the number of imaging, the interval of imaging, the duration of imaging, and so on. If a plurality of imaging conditions is configured, there will be a plurality of NIOs corresponding thereto.

The NIO is configured by some basic NIOs. For example, the NIO for a simple X-ray imaging is composed of a basic NIO for one single X-ray exposure and the data acquisition for one time, and of another basic NIO for the data transfer for one time. The NIO for the fluoroscopy that is comprised of for example 20 frames of the first half in a two seconds interval and of 30 frames of the second half in a ten seconds interval, is composed of 50 basic NIOs for the X-ray exposure and the data acquisition and 50 basic NIOs for the data transfer, as well as a basic NIO for the idling of 340 seconds.

The required power for each basic NIO, $\Delta RSOC$ is held in the $\Delta RSOC$ table 406. Now referring to FIG. 7 there is shown the structure of the $\Delta RSOC$ table 406. As shown in FIG. 7 the $\Delta RSOC$ table 406 holds the required power $\Delta RSOC$ #1 to #n for a plurality of basic NIO #1 to #n.

The $\Delta RSOC$ table 406 is stored for example in a non-volatile memory so as to hold the contents even when the power is shut down. In a non-volatile memory the basic NIO #1 to #n correspond to the addresses, and the required power $\Delta RSOC$ #1 to #n correspond to the contents.

The $\Delta RSOC$ table 406 may be masked by the user if needed. In the masked $\Delta RSOC$ table 406 all data is 0. The $\Delta RSOC$ table 406 is an exemplary memory device in accordance with the present invention.

The required power $\Delta RSOC$ for each basic NIO is determined beforehand by the actual measurement. The required power $\Delta RSOC$ for each basic NIO is appropriately updated by the update unit 408. The update unit 408 is an exemplary memory update device in accordance with the present invention.

The threshold calculation unit 402a reads out the required power for the basic NIOs composing the NIO from the $\Delta RSOC$ table 406, and then calculates the threshold by multiplying the sum of the power with a coefficient. The index is a number greater than 1. The part of the value beyond 1 is a margin for giving the room to the required power. If no margin is required the coefficient may be set to 1. The threshold calculated by the threshold calculation unit 402a is used for the threshold for determining whether or not the initial operation of NIO is executable.

The threshold for determining whether or not the subsequent operation of NIO is acceptable is calculated by the threshold calculation unit 402b. The threshold calculation unit 402b calculates the difference between the RSOC measurement value before NIO execution and the value after NIO execution, then calculates the threshold by multiplying the difference with the coefficient as have been described above.

Figure 8:
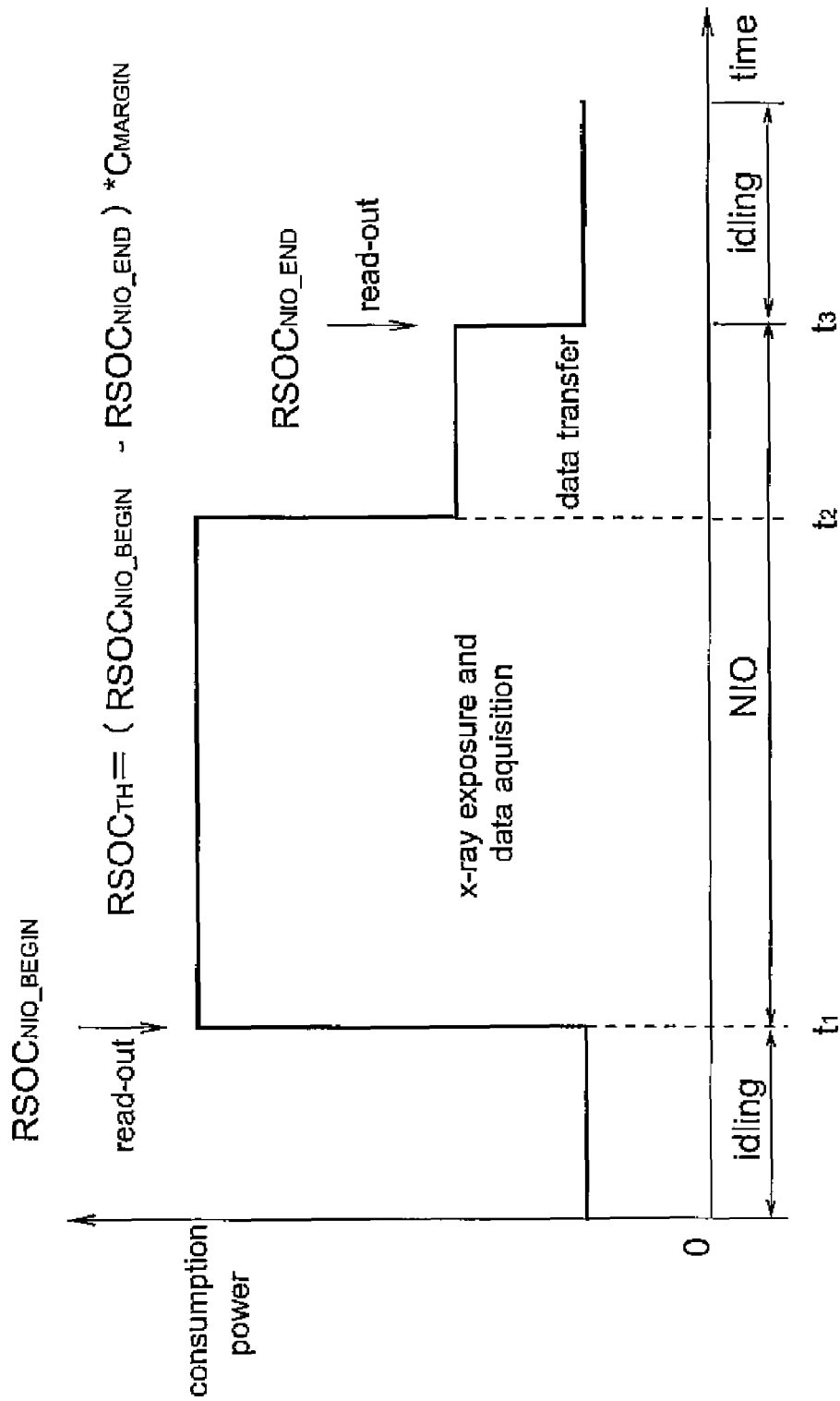
FIG. 8 is a schematic diagram illustrating an example of threshold calculation by the threshold calculation unit.

Now referring to FIG. 8 there is shown an example of threshold calculation by the threshold calculation unit 402b. As shown in FIG. 8, assuming that at the time of a simple X-ray imaging, the X-ray exposure and data acquisition is performed in the time ranging from t1 to t2, the data is transferred in the time ranging from t2 to t3, and the current is consumed in both periods of time, the measurement value of the remaining power $RSOC_{NIO\text{-}BIGIN}$ at the time t1 and the measurement value of the remaining power $RSOC_{NIO\text{-}END}$ at the time t3 are read out, and the threshold $RSOC_{TH}$ is calculated by multiplying the difference therebetween with the coefficient $C_{MARGIN}$.

Figure 9:
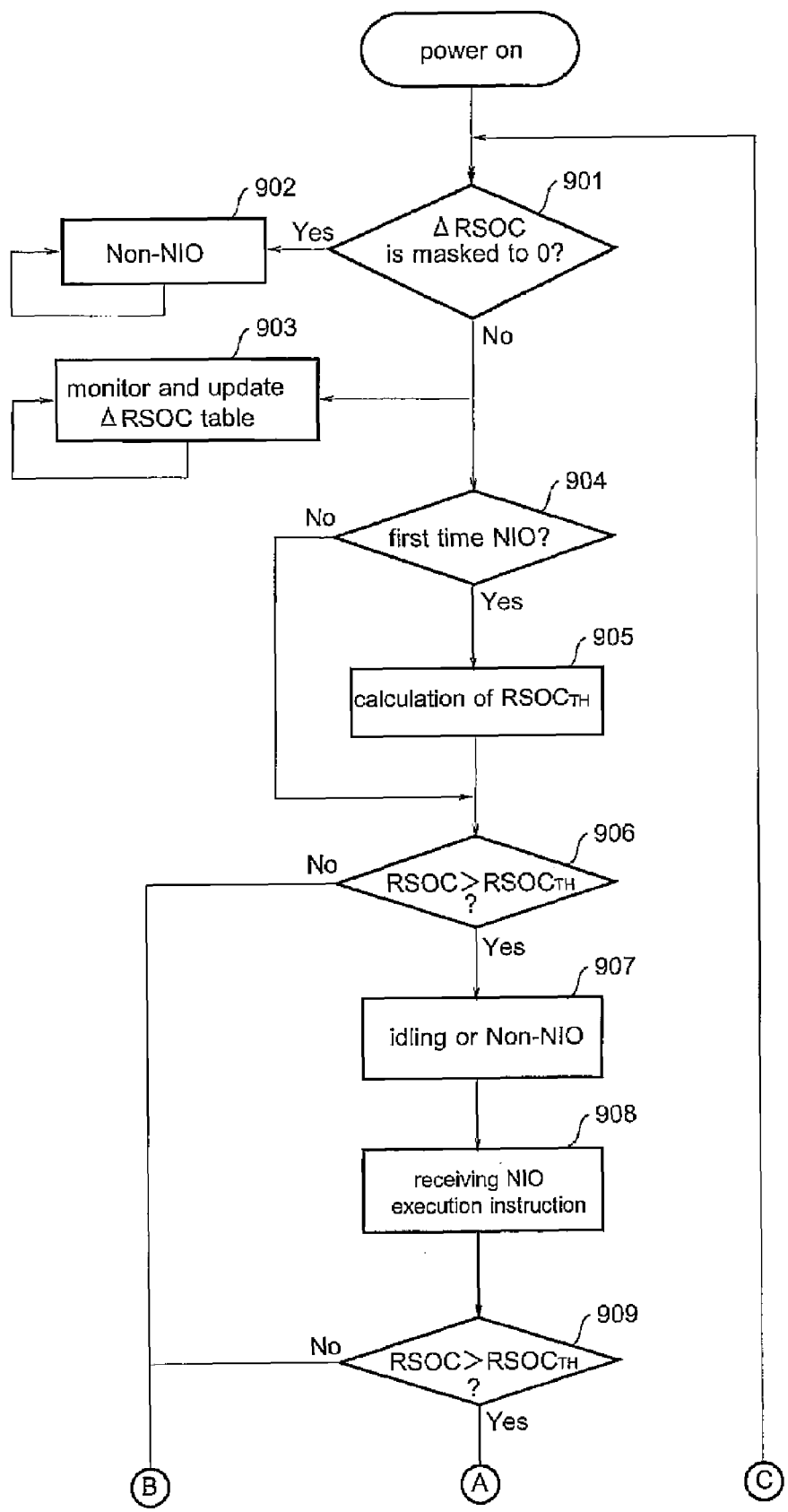
FIG. 9 is a schematic flow diagram illustrating the operation management.
Figure 10:
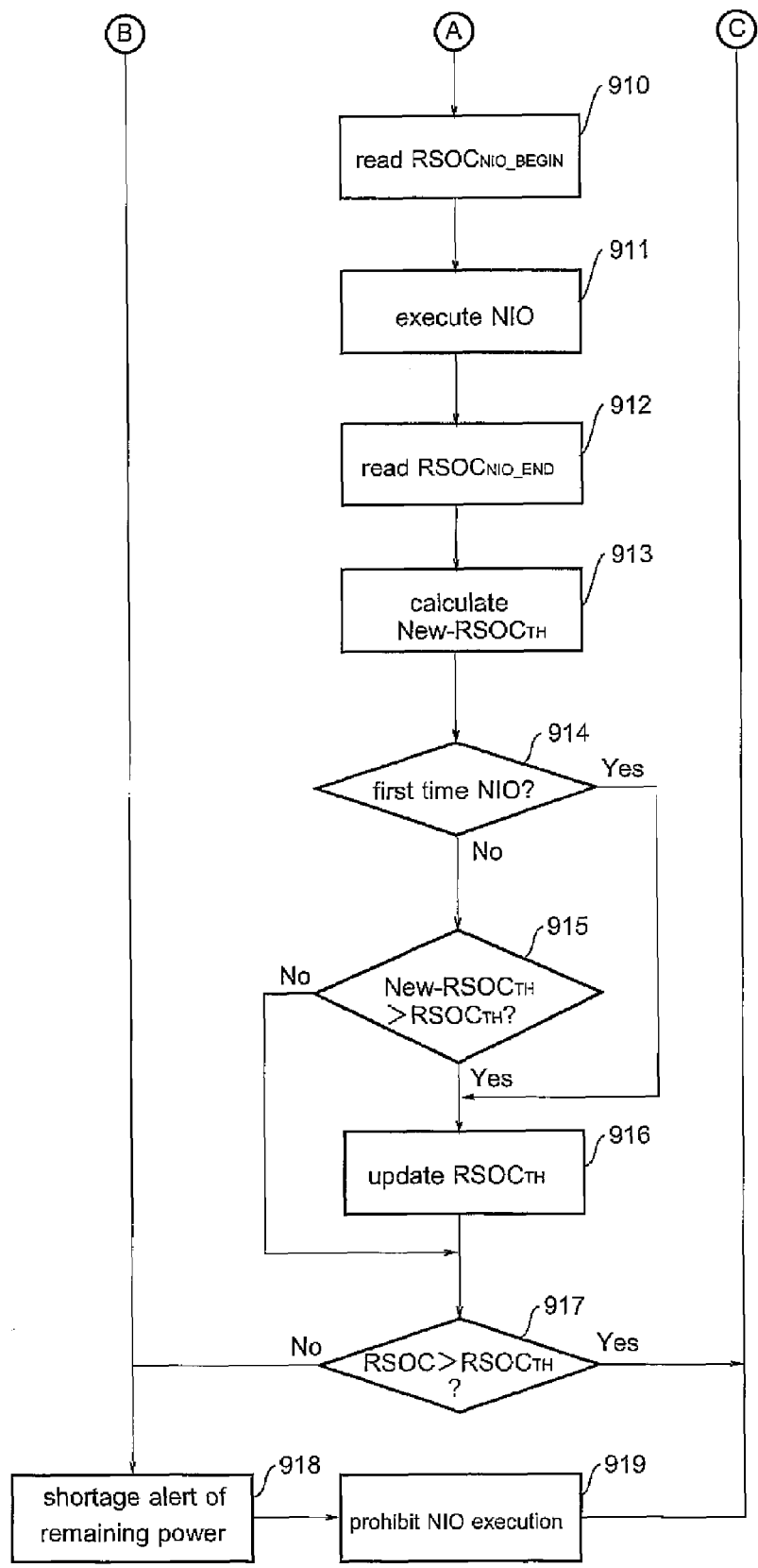
FIG. 10 is a schematic flow diagram illustrating the operation management.

Now referring to FIG. 9 and FIG. 10 there are shown a first half and a second half of the schematic flow diagram of the operation of the detector panel 200. The operation is substantially that of the circuit for operation management 208. As shown in FIG. 9, at the time of power on, in step 901, the $\Delta RSOC$ table is determined whether masked to 0 or not.

If the $\Delta RSOC$ table is masked to 0, then in step 902 the state is Non-NIO. If the $\Delta RSOC$ is not masked then in step 903 the $\Delta RSOC$ table is monitored and updated. The monitoring and update of the $\Delta RSOC$ table is performed in the background.

In the foreground, in step 904, the NIO is determined whether it is for the first time or not. If it is the first time NIO, then in step 905 the $\Delta RSOC$ table is used to calculate the threshold $RSOC_{TH}$. The calculation of the threshold $RSOC_{TH}$ is performed by the threshold calculation unit 402a. If the NIO is not the first time NIO, then the NIO is that performed in the immediately previous time, and the threshold $RSOC_{TH}$ is already calculated so that the step 905 is skipped.

In step 906 it is determined if the current remaining power RSOC is above the threshold $RSOC_{TH}$ or not. If the current remaining power RSOC is not above the threshold $RSOC_{TH}$, then in step 918 the shortage alert of required power is sounded. The shortage alert of power is transferred through the interface circuit 206 to the system console 100, and is also displayed on the display of the detector panel 200.

After the transfer and/or display of the shortage alert of power, in step 919, the execution of NIO is prohibited. If the current remaining power RSOC is not above the threshold $RSOC_{TH}$, there is a risk that the operation may be stopped prior to completion because of the shortage of the power left in the battery when the NIO is executed. However such a situation may be prevented by prohibiting beforehand the execution of the NIO. In accordance with the shortage alert of the remaining power, the battery may be recharged or replaced earlier than a trouble.

If the current remaining power RSOC is above the threshold $RSOC_{TH}$, in step 907 the operation is in idling or Non-NIO state. In this situation in step 908, a NIO execution instruction is received, and in step 919 the current remaining power RSOC is once again determined whether to be above the threshold $RSOC_{TH}$ or not.

If the current remaining power RSOC is not above the threshold $RSOC_{TH}$, then in step 918 a shortage alert of remaining power is sounded, in step 909 the execution of the NIO is prohibited. By doing this any futile operation immediately before executing the NIO may be avoided.

If the current remaining power RSOC is above the threshold $RSOC_{TH}$, then in step 910 the measurement value of the remaining power $RSOC_{NIO\text{-}BIGIN}$ is read out, then in step 911 the NIO is executed. After executing the NIO in step 912, the measurement value of the remaining power $RSOC_{NIO\text{-}END}$ at that state is read out.

In step 913 a new threshold New-$RSOC_{TH}$ is calculated. The calculation of the new threshold New-$RSOC_{TH}$ is performed by the threshold calculation unit 402b, based on the difference between the measurement value of the remaining power $RSOC_{NIO-BIGIN}$ at the time of start of the NIO and the measurement value of the remaining power $RSOC_{NIO-END}$ at the time of end of the NIO.

In step 914 it is determined whether it is a first time NIO or not. If it is a first time NIO then in step 916 the threshold $RSOC_{TH}$ is updated. By doing this a new threshold value New-$RSOC_{TH}$ becomes the threshold for this NIO for the next time.

If the NIO is not for the first time, then the NIO is that executed in the last time, and in step 915 the threshold New-$RSOC_{TH}$ is determined whether or not to be above the threshold $RSOC_{TH}$ used so far (the threshold for the last time), and if the threshold is above then in step 916 the threshold $RSOC_{TH}$ is update, otherwise if the threshold is not above then the step 916 is skipped. By doing this the threshold New-$RSOC_{TH}$ is update only when it is above the threshold $RSOC_{TH}$ used before, if the NIOs not for the first time.

By the threshold update as have been described above, the operation management of the detector panel 200 is performed without affected by the aging of the battery, in other words the decrease of capacity along with the repetition of recharging and discharging.

In step 917 the current remaining power RSOC is once again determined whether or not to be above the threshold $RSOC_{TH}$. If the current remaining power RSOC is not above the threshold $RSOC_{TH}$, then in step 918 a shortage alert of remaining power is sounded, and the execution of the NIO is prohibited in step 919. By doing this the execution of the NIO for the next time is prohibited, allowing avoiding any futile operation without waiting for the determination immediately prior to the operation.

If the current remaining power RSOC is above the threshold RSOCTH, the process goes back to step 901. The process followed by the step 901 will be repeated for the same NIO or for the first time NIO.

What is claimed is:

1. An X-ray imaging apparatus comprising:
    a system console comprising an X-ray emitter and a control circuit; and
    a detector panel comprising:
        an X-ray detector;
        an electronic circuit for interface;
        a battery for power supply;
        a measurement device configured to measure an amount of electric power left in said battery; and
        a determination device configured to determine whether execution of an operation is possible based on a comparison of the electric power left in said battery with a threshold defined in accordance with a required amount of electric power for operating said X-ray detector and said electronic circuit.

2. An X-ray imaging apparatus according to claim 1, wherein the operation is not interruptible.

3. An X-ray imaging apparatus according to claim 1, further comprising:
    a memory device configued to store the required amount of electric power for each unit operation constituting the operation.

4. An X-ray imaging apparatus according to claim 3 further comprising:
    a memory update device configured to update stored values in said memory device.

5. An X-ray imaging apparatus according to claim 3, further comprising:
    a first threshold calculation device configured to determine an initial value of the threshold based on stored values prior to initial execution of the operation.

6. An X-ray imaging apparatus according to claim 1, further comprising:
    a second threshold calculation device configured to determined a latest threshold based on the measured amount of electric power left before and after the execution of the operation.

7. An X-ray imaging apparatus according to claim 6, further comprising:
    a threshold update device configured to update the threshold using the latest threshold.

8. An X-ray imaging apparatus according to claim 7, wherein the update of the threshold is performed when the latest threshold is larger than the prior threshold.

9. An X-ray imaging apparatus according to claim 1, wherein the comparison is performed prior to the execution of the operation.

10. An X-ray imaging apparatus according to claim 9, wherein the comparison is performed after the execution of the operation.

11. A detector panel comprising:
    an X-ray detector;
    an electronic circuit for interface;
    a battery for power supply;
    a measurement device configured to measure an amount of power left in said battery; and
    a determination device configured to determined whether an operation is executable based on a comparison of an amount of power left in said battery with a threshold determined based on a required amount of power for operating said X-ray detector and said electronic circuit.

12. A detector panel according to claim 11, wherein the operation is not interruptible.

13. A detector panel according to claim 11, further comprising:
    a memory device configured to store a required amount of power for each unit operation constituting the operation.

14. A detector panel according to claim 13, further comprising:
    a memory update device configured to update stored values in said memory device.

15. A detector panel according to claim 13, further comprising:
    a first threshold calculation device configured to determine an initial value of the threshold based on stored values prior to initial execution of the operation.

16. A detector panel according to claim 11, further comprising:
    a second threshold calculation device configured to determine a latest threshold based on the measured amount of power left before and after the execution of the operation.

17. A detector panel according to claim 16, further comprising:
    a threshold update device configured to update the threshold using the latest threshold.

18. A detector panel according to claim 17, wherein the update of the threshold is performed when the latest threshold is larger than the prior threshold.

19. A detector panel according to claim 11, wherein the comparison is performed prior to the execution of the operation.

20. A detector panel according to claim 19, wherein the comparison is also performed after the execution of the operation.

* * * * *